United States Patent
Bailey et al.

(10) Patent No.: US 8,420,857 B2
(45) Date of Patent: Apr. 16, 2013

(54) REMOVAL OF SILICA FROM WATER SOLUBLE COMPOUNDS BY NANOFILTRATION AND REVERSE PHASE CHROMATOGRAPHY

(75) Inventors: Allan R. Bailey, Ballwin, MO (US); David H. White, Ballwin, MO (US); Derick L. Kaspar, Webster Groves, MO (US); Robert E. Vandas, Florissant, MO (US); Michael J. Gentilcore, Maryland Heights, MO (US); Hung V. Nguyen, Florissant, MO (US); Anna K. Fukunaga, Florissant, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 342 days.

(21) Appl. No.: 12/675,130

(22) PCT Filed: Aug. 21, 2008

(86) PCT No.: PCT/US2008/073796
§ 371 (c)(1),
(2), (4) Date: Nov. 29, 2010

(87) PCT Pub. No.: WO2009/029464
PCT Pub. Date: Mar. 5, 2009

(65) Prior Publication Data
US 2011/0065959 A1 Mar. 17, 2011

Related U.S. Application Data

(60) Provisional application No. 60/966,273, filed on Aug. 27, 2007.

(51) Int. Cl.
*C07C 231/24* (2006.01)

(52) U.S. Cl.
USPC .......................................................... 564/153

(58) Field of Classification Search ................... 564/153
See application file for complete search history.

(56) References Cited

U.S. PATENT DOCUMENTS

| | | |
|---|---|---|
| 5,160,437 A | 11/1992 | Bosworth et al. |
| 5,191,120 A | 3/1993 | Kneller et al. |
| 5,204,005 A | 4/1993 | Doran, III et al. |
| 5,447,635 A | 9/1995 | Viscardi et al. |
| 5,811,581 A | 9/1998 | Piva et al. |
| 6,066,259 A | 5/2000 | Viscardi et al. |

FOREIGN PATENT DOCUMENTS

WO WO 97/30735 8/1997

OTHER PUBLICATIONS

Drews et al., "Nanofiltration of CIP waters from iodine X-ray contrast media production: process design and modeling", Desalination, vol. 159, 2003, pp. 119-129.

*Primary Examiner* — Shailendra Kumar

(57) ABSTRACT

A process for separating soluble silica species such as monomeric silicic acid (or monosilicic acid) and low molecular weight soluble polymeric silica from impure water soluble compounds by membrane nanofiltration is provided. A process for separating soluble silica species and colloidal silica from impure water soluble compounds by reverse phase liquid chromatography is also provided.

45 Claims, No Drawings

REMOVAL OF SILICA FROM WATER SOLUBLE COMPOUNDS BY NANOFILTRATION AND REVERSE PHASE CHROMATOGRAPHY

CROSS REFERENCE TO RELATED APPLICATIONS

This application is a national stage application of PCT/US2008/073796, filed Aug. 21, 2008, which claims the benefit of U.S. Provisional Application No. 60/966,273 filed Aug. 27, 2007.

FIELD OF THE INVENTION

The present invention generally relates to processes for the removal of monosilicic acid, soluble polymeric silica and colloidal silica from water soluble compounds.

BACKGROUND OF THE INVENTION

Chemically modified silicas are widely used as packing supports in chromatographic separations for the purification of water soluble products. Generally, modified silica packings comprise derivatized silicas to which organic substituents, such as alkyl chains, have been attached. Those packings can deteriorate and release silica as a contaminant into purified products as a result of chemical attack by the mobile phase. Problematic mobile phases include water, low molecular weight alcohols, and mobile phases having a pH outside the range of about 2 to about 7.

It has heretofore been accepted that the release of silica into purified products is an unavoidable consequence of the packing's ability to perform properly in chromatographic purification processes. In situations where silica content must be reduced to meet product specifications, such as for pharmaceutical compounds, ion exchange resins have been used to remove silica. See U.S. Pat. No. 5,204,005 to Doran, et al. However, soluble polymeric or colloidal silica removal by ion exchange chromatography is undesirable because resins must be regenerated, a process step that generates waste streams is added, operating costs are increased, and capital expenditure is required. In addition, ion exchange chromatography exposes the desired product to extremes of pH which may be undesirable for x-ray contrast media and is prohibited for MRI agents.

A need remains for processes for the efficient and cost effective removal of silica from water soluble products.

SUMMARY OF THE INVENTION

Among the various aspects of the present invention is the provision of an improved process for the removal of monosilicic acid, soluble polymeric silica and colloidal silica from water soluble compounds.

Briefly, therefore, one aspect of the present invention is a process for purifying a product solution comprising a product compound, and silica species selected from at least one of soluble monosilicic acid, soluble polymeric silica or colloidal silica. The process comprises processing the product solution in a nanofiltration membrane apparatus to separate the product solution into a permeate stream comprising silica species having a molecular weight below the molecular weight cut-off of the membrane and a retentate stream comprising the product compound and silica species having a molecular weight above the molecular weight cut-off of the membrane.

The present invention is further directed to a process for purifying a product solution comprising a product compound and polymeric silica. The process comprises loading the product solution on a reverse phase chromatographic apparatus containing a silica-based stationary phase and eluting one or more pre-fraction streams and one or more purified product fraction streams. The polymeric silica contained in the sum of the pre-fraction streams is thereby concentrated with reference to the sum of the purified product fraction streams and the purified product compound contained in the sum of the purified product fraction streams is concentrated with reference to the sum of the pre-fraction streams.

The present invention is further directed to a process for purifying a product solution comprising a product compound and polymeric silica. The process comprises loading the product solution on a reverse phase chromatographic apparatus containing a stationary phase and forming by separation a product compound stream comprising the product compound and a polymeric silica stream comprising the polymeric silica.

DESCRIPTION OF THE PREFERRED EMBODIMENTS

The present invention is directed to a process for separating monomeric silicic acid (or monosilicic acid) and low molecular weight soluble polymeric or colloidal silica from impure water soluble compounds by membrane nanofiltration. The present invention is further directed to a process for separating soluble silica species and colloidal silica from impure water soluble compounds by reverse phase liquid chromatography with suitable silica-backbone chromatography packing.

The process of the present invention is useful for removing soluble silicon species such as silica, monosilicic acid, polymeric silica and colloidal silica from impure water soluble compounds having a molecular weight in excess of about 400. In one embodiment, the water soluble compound is a nonionic or ionic pharmaceutical chemical, particularly those that are purified using reverse phase liquid chromatography with water and/or low molecular weight alcohol solvent systems. An example of such pharmaceutical chemicals are peptides purified using reverse phase liquid chromatography. In another embodiment, the pharmaceutical chemical is a radiographic nonionic contrast media compound. In another embodiment, the radiographic nonionic, iodinated contrast media compound is an x-ray contrast agent. Examples of such x-ray contrast agents include, without limitation, iopamidol, iomeprol, iohexyl, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. The currently preferred x-ray contrast agents include iopamidol, iomeprol, iohexyl, ioversol, iodixanol, iotrolan and iosimenol. In still another embodiment, the pharmaceutical chemical is a magnetic resonance imaging (MRI) contrast agent, particularly those containing a lipophilic component. Examples of such MRI agents include, without limitation, gadofosveset trisodium (diphenylcyclohexyl phosphodiester-Gd-DTPA), gadoxdetate (Gd-ethoxybenzyl-DTPA), gadomelitol, gadobenate dimeglumine, and the corresponding ligands thereof.

Synthetic processes for the preparation of some water soluble compounds often involve complex chemistry, multiple steps, and numerous reagents and byproducts. The net result is impurities are present in the compounds that are difficult to remove in an efficient and economical manner. Chromatographic methods such as reverse phase liquid chromatography ("LC") are widely used for removing structurally related impurities from water soluble compounds. In general, impurities elute in one or more LC pre-fraction streams and the water soluble compounds subsequently elute in one or more LC purified product fraction streams. In many cases, a stationary phase comprising a derivatized silica backbone is used. Examples of silica-based stationary phases include, for instance, alkylsilanes, arylsilanes and haloalkylsilanes. Problematically, aqueous mobile phases, alcoholic mobile phases and mobile phases having a pH outside the range of about 2 to about 7 can hydrolytically attack the siloxane bonds (Si—O—Si) in the underlying silica backbone thereby resulting in the generation and release of monosilicic acid ($Si(OH)_4$) that dissolves into water soluble product chromatographic fraction streams. Aqueous mobile phases include, without restriction, deionized water, distilled water, buffer solutions and aqueous solutions containing salts. Alcoholic mobile phases generally comprise $C_{1-4}$ alcohols and mixtures thereof. In embodiments where alcohol purity is less than 100%, the mobile phase generally comprises an admixture of an aqueous mobile phase and an alcoholic mobile phase.

Dissolved $Si(OH)_4$ can polymerize in product fraction streams into larger molecules including soluble polymeric silica, colloidal silica and silica particles. $Si(OH)_4$ is relatively stable in solution at neutral pH below its solubility limit, with silica solubility depending on pH, temperature and composition of the product stream. At $Si(OH)_4$ concentrations beyond the solubility limit, the $Si(OH)_4$ molecules begin forming siloxane bonds (Si—O—Si) thereby making oligomers and polymers of $Si(OH)_4$ such as soluble silica polymers, and colloidal solutions and/or silica gels that are weakly soluble or insoluble in water. Polymerization can continue resulting in the formation of insoluble silica particles. Polymerization generally proceeds according to reaction (1):

$$Si(OH)_4 + Si(OH)_4 \rightarrow (OH)_3Si-O-Si(OH)_3 + H_2O \qquad (1)$$

Longer chain polymers can be formed according to reaction (2):

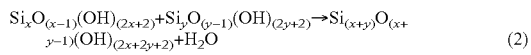

$$Si_xO_{(x-1)}(OH)_{(2x+2)} + Si_yO_{(y-1)}(OH)_{(2y+2)} \rightarrow Si_{(x+y)}O_{(x+y-1)}(OH)_{(2x+2y+2)} + H_2O \qquad (2)$$

$Si(OH)_4$ polymerization kinetics are generally affected by initial silicic acid concentration, temperature, time, pH and/or the presence of ions that may exert a catalytic influence or increase the ionic strength of the solution. However, colloidal silica is typically not formed during typical process scenarios where the pH is approximately neutral, the silicic acid concentration is not high, for example not greater than about 2000 µg $SiO_2$ per mL, and total processing times are on the order of less than about 24 hours. For example, at a pH of about 3, about 100 hours are required to increase the silica polymer molecular weight from about 160 to about 1500. Colloidal silica formation typically occurs after long term storage or during subsequent processing, such as during drying operations.

The water soluble compounds of the present invention typically have an upper specification limit for silica content, usually expressed on a weight per weight or weight percent basis. In the case of a lower specification limit for silica content, the water soluble compounds of the present invention would typically have a lower specification limit of 0, Silica concentration is controlled during the process of the invention to keep the ratio of silica to product molecule below the upper specification limit. Silica specification limits can suitably vary from less than about 0.5 weight percent ("wt %"), less than about 0.1 wt %, less than about 0.05 wt %, less than about 0.01 wt % to even less than about 0.005 wt %. In the case of pharmaceutical compounds, the specification limit typically varies based on the route of administration with topicals generally having the highest limit, enterals having a lower limit and parenterals having the lowest limit. In the case of MRI or iodinated x-ray contrast agents, the limit can be, for example, less than or equal to 500 µg of silica per gram of compound (≦0.05 weight percent), less than or equal to 200 µg of silica per gram of compound (≦0.02 weight percent) to less than or equal to 50 µg of silica per gram of compound (≦0.005 weight percent).

For a given process for purifying water soluble products by LC, the mobile phase composition, the stationary phase, temperature and ionic strength are generally fixed within narrow ranges resulting in a relatively consistent rate of $Si(OH)_4$ dissolution into the mobile phase (i.e., eluent) containing the water soluble product. For a given process therefore, eluent $Si(OH)_4$ concentration within a range is typically consistent and predictable. For instance, experimental evidence to date indicates that impure water soluble compounds processed by liquid chromatography using a 45° C. aqueous mobile phase having a pH of from about 2 to about 7 and a stationary phase comprising $C_8$ double-end capped packing having a silica backbone results in a silica concentration of about 2000 µg $SiO_2$/mL. Any conventional quantitative method known to those of ordinary skill in the art that can be used for measuring silica content, e.g., light scattering, spectroscopic methods (for instance inductively coupled plasma ("ICP") spectroscopy) and derivatization methods, is suitable for determining silica concentration.

In a first purification embodiment of the present invention, it has been discovered that dissolved $Si(OH)_4$, certain dissolved short chain soluble $Si(OH)_4$ polymers, and certain low molecular weight colloidal silica can be separated from chromatographic product fraction streams using nanofiltration ("NF"), thereby purifying the product to silica levels at or below the silica upper specification limits disclosed above.

NF methods are known in the art. See, for example, U.S. Pat. No. 5,160,437 to Bosworth, et al. and U.S. Pat. No. 5,447,635 to Viscardi. et al. In NF, a chromatographic product fraction containing one or more silicon species is contacted with a semi-permeable membrane at elevated pressure. A portion of the dissolved $Si(OH)_4$, certain dissolved short chain soluble $Si(OH)_4$ polymers, and certain low molecular weight colloidal silica pass through the membrane with a portion of the mobile phase in a permeate stream and are thereby concentrated in the permeate stream. The water soluble product, long chain soluble $Si(OH)_4$ polymers and colloidal silica that do not pass through the membrane (i.e., are "rejected") are thereby concentrated in a retentate stream. The permeate and retentate streams can be processed in continuous or discontinuous diafiltration mode to further concentrate their respective components. In continuous diafiltration, the impure product stream is maintained at a fixed volume while it is contacted under pressure with the filtration membrane. In discontinuous diafiltration, silica contaminants are removed by repeated concentration and dilution. It is typical to perform multiple diafiltrations to achieve the desired results, e.g. 3 to 15 diafiltrations. It is preferred to perform 5, 6, 7, 8, 9, 10, 11, 12, 13, 14 or even 15 diafiltrations.

NF is generally classified based on the molecular weight cut-offs of the membrane. Generally, membrane selection depends on the molecular weight of the water soluble product compound. NF membranes suitable for the present invention typically have a molecular weight cut-off of about 200 to about 2000 Daltons. In one embodiment, the NF membranes suitable for the present invention have a molecular weight cut-off of about 400 to about 1000 Daltons. The nominal pore diameter of typical NF membranes is from about 10 Å to about 100 Å, but the molecular weight cut-off is the currently preferred membrane selection criteria. Generally, the largest pore size that will provide at least 95%, 96%, 97%, 98%, or 99% product compound retention is preferred. Typical NF membranes reject solutes (i.e., product compounds) having a molecular weight in the range in excess of about 300 grams per mol ("g/mol"). In order to maximize water soluble product rejection rate, and therefore minimize product losses, membranes having a selectivity of about 50 to 80 percent, or about 60 to 70 percent, of the object water soluble compound molecular weight is selected. In one embodiment, water soluble products having a molecular weight in the range of about 600 to about 900 g/mol, such as, for example the x-ray contrast agents ioversol (807 g/mol), iohexyl (821 g/mol), metrizamide (789 g/mol), iopentol (835 g/mol), iopromide (791 g/mol) and iotrolan (626 g/mol), are purified using NF filters having a molecular weight cut off of about 350 to about 400 g/mol. In another embodiment, water soluble products having a molecular weight in the range of about 1400 to about 1650 g/mol, more particularly about 1500 g/mol, such as, for example the MRI agents, iodixanol (1550 g/mol), iosimenol (1478 g/mol) and iotrolan (1626 g/mol) may be purified using NF filters having a molecular weight cut off of about 1000 g/mol.

In addition to pore size, filtration membrane material of construction and configuration should be considered. Membranes should be solvent stable and swell no more than about 10% when immersed in the mobile phases used in connection with the present invention. Membrane swelling can result in increased pressure drop and power consumption, and premature membrane fouling. Solvent-mediated membrane degradation can result in membrane failure by tearing or rupture and/or effective pore size increase with resulting decreased rejection rate and increased product losses.

In product purification by NF, the amount of silica rejected in NF and thereby concentrated in the retentate stream with the water soluble compounds should not exceed the specification limit. In accordance with the present invention, the impure water soluble product stream is evaluated to estimate the silica concentration in order to determine NF purification conditions required to purify the impure product sufficiently to meet the required silica limit. Silica removal by NF purification is then done. The impure water soluble product stream can be an LC product fraction stream or other process streams comprising a water soluble product and a silica contaminant. In a first evaluation method, the silica content of an impure product stream can be estimated from historical values or experimentally determined values for particular mobile phase-stationary phase systems. Based on the estimated silica content and known silica rejection rates for particular membranes, the number of wash volumes required to purify the product to the required silica content can be determined. For example, if the NF rejection rate is 50%, assuming exponential decay, 5 wash volumes would be required to remove about 95 to about 98% of the contained silica. In a second evaluation method, the silica content of the impure product stream can be measured by any quantitative method known in the art such as, for example, ICP spectroscopy. As described above, from the measured silica level and a known NF rejection rate, the number of NF wash volumes required to meet the silica limit can be determined. In a third evaluation method, during NF purification, the water soluble product retentate stream can be periodically or continuously measured by, for example, ICP spectroscopy to determine when the silica limit has been met. At least about 70%, 80%, 90%, 91%, 92%, 93%, 94%, 95%, 96%, 97%, 98% or even 99% of the monosilicic acid, poly-meric silica and colloidal silica having a molecular weight less than the molecular weight cut-off of a particular NF membrane can be separated and removed by NF.

In a second purification embodiment of the present invention, it has been discovered that colloidal silica and high molecular weight polymeric silica that typically cannot be removed by NF purification can be separated from water soluble products using LC. Therefore, finished product silica specifications can be met by performing LC purification (i) if the silica concentration remaining in the NF retentate is above the silica specification limit or (ii) if after processing, such as, for example, water soluble product concentrating or drying, silica species are formed that could not be effectively removed by NF purification. Silica-based stationary phases as previously described have been discovered to be effective for removing silica species including soluble polymeric silica and colloidal silica from the water soluble products of the present invention. The silica species elute from the column in a pre-fraction before elution of the water soluble compounds. In one aspect of this embodiment, the impure water soluble product can be rerun through the same stationary phase used in the initial LC purification and without adjustment to the mobile phase. In other words, the impure water soluble product can be recycled batch-wise through the LC column in order to remove silica species. In another aspect of this embodiment, a silica-based stationary phase resistant to silica leaching can be used for silica species removal thereby minimizing silica contamination. It has been discovered that LC is efficient at removing silicon species from water soluble products that are typically not removable by NF, such as large molecular weight silica polymers and colloidal silica. In silica removal by LC, the weight ratio of the silica contained in the sum of the LC pre-fraction streams to the silica contained in the sum of the LC purified product fraction streams is at least about 2:1, 5:1, 10:1, 20:1, 30:1, 40:1, 50:1 or even 100:1. Stated differently, at least about 70%, 80%, 90%, 91%, 92%, 93%, 94%, 95%, 96%, 97%, 98% or even 99% of the silicon species present can be separated and removed by LC.

Although silicon species are removed by LC, $Si(OH)_4$ may nonetheless dissolve once again into the mobile phase. Over time silica polymerization and colloid formation could once again occur. Therefore, even if removal of silicon species by LC is done, it is preferred to perform NF purification as soon as practical after completion of LC in order to remove monomeric silicic acid and thereby prevent significant formation and accumulation of colloidal silica.

Having described the invention in detail, it will be apparent that modifications and variations are possible without departing from the scope of the invention defined in the appended claims.

EXAMPLES

The following non-limiting examples are provided to further illustrate the present invention.

Example 1

A solution containing 427 mg/mL of iosimenol and containing 3979 μg $SiO_2$ per gram of iosimenol was passed through double-end cap C8 packing (Mallinckrodt Baker, Inc. BAKERBOND™ Reverse Phase Chromatography Media Product Number 7637) in an LC column at a load ratio of 13:1. 5500 g of the C8 packing were packed into a preparative scale column, d=20.32 cm and h=31.75 cm. Methanol was pumped through the column at 1.2 L/min to wet the packing. The column was equilibrated with water by pumping water through the column at 1.2 L/min. 1000 mL of impure iosimenol solution (427 mg/mL) were pumped onto the column at 1.2 L/min and the iosimenol was purified by flowing water through the column at 1.2 L/min. Five fractions of varying volume were collected. The eluent was process water at about 45° C. Samples were collected during water equilibration of the column and pre- and post-fraction collection, and analyzed for silica and iosimenol concentrations. Iosimenol concentration was determined using HPLC and silica concentration was determined using ICP atomic absorption. The results are presented in Tables 1-3.

TABLE 1

LC Data for Iosimenol Purification

| Fraction | Volume (L) | Iosimenol (mg/mL) | Iosimenol (g) |
|---|---|---|---|
| F1 | 4 | 6.8 | — |
| F2 | 20 | 13.3 | 266 |
| F3 | 20 | 5.4 | 107 |
| F4 | 20 | 1.5 | 31 |
| F5 | 20 | 0.5 | 10 |

| Fraction | Cumulative Purity | Cumulative Yield | Cumulative Volume (L) |
|---|---|---|---|
| F1 | — | — | — |
| F2 | 97.1 | 63 | 20 |
| F3 | 97.4 | 88.4 | 40 |
| F4 | 97.3 | 95.7 | 60 |
| F5 | 97.1 | 98.1 | 80 |

TABLE 2

Silica Results for Iosimenol Purification

| Sample | Iosimenol (mg/mL) | $SiO_2$ (µg/g) | Iosimenol (g) |
|---|---|---|---|
| Chromatography Feed | 427 | 3979 | 425 |
| Combined F2-F5 Fractions | 227 | 32 | 250 |

| Sample | pH | $SiO_2$ (µg/mL) | Volume (L) | $SiO_2$ (mg) |
|---|---|---|---|---|
| Chromatography Feed | 7 | 1699 | 1 | 1700 |
| Combined F2-F5 Fractions | 7.6 | 7 | 1.1 | 8 |

TABLE 3

Water Equilibration and Pre- and Post-Fraction Collection Silica Data

| Sample | $SiO_2$ (µg/mL) | Volume (L) | $SiO_2$ (mg) |
|---|---|---|---|
| Water Equil. 1 | 8 | N/A | N/A |
| Water Equil. 1 | 11 | N/A | N/A |
| Water Equil. 1 | 13 | 30 | 390 |
| Pre 1 | 86 | 20 | 1720 |
| Fraction F1 | 14 | 4 | 56 |
| Post 1 | 6 | 22 | 132 |

Fractions F2-F5 were combined and concentrated by NF. Fractions F2-F5 were sequentially added to the NF feed tank and NF performed until the combined batch was at the desired concentration. The final silica concentration for combined fractions F2-F5 was 32 µg/g of iosimenol which meets the product specification of ≦50 µg silica/g iosimenol. The total silica reduction was 99%. The data in Tables 2 and 3 suggest that substantially all the silica was removed in the Pre 1 stream. Approximately 1700 mg of silica was present in the feed solution (Table 2-chromatography feed) and approximately 1700 mg of silica was collected in the Pre 1 stream (Table 3).

The Example 1 results demonstrate that double-end cap C8 reverse phase chromatography packing is effective at removing soluble polymeric and colloidal silica. The silica species were removed in the pre-fraction collected prior to product elution.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above methods and processes without departing from the scope of the invention, it is intended that all matter contained in the above description shall be interpreted as illustrative and not in a limiting sense.

What is claimed is:

1. A process for purifying a product solution comprising a product compound and a silica species selected from at least one of soluble mono silicic acid, soluble polymeric silica and colloidal silica, the process comprising:
   processing the product solution in a nanofiltration membrane apparatus to separate the product solution into a permeate stream comprising silica species having a molecular weight below the molecular weight cut-off of the membrane and a retentate stream comprising the product compound and silica species having a molecular weight above the molecular weight cut-off of the membrane; and,
   loading the retentate stream on a chromatographic apparatus containing a stationary phase and separating the product compound from the silica species having a molecular weight above the molecular weight cut-off of the membrane to form a chromatographic product compound stream and a chromatographic silica stream containing the silica species having a molecular weight above the molecular weight cut-off of the membrane.

2. The process of claim 1 wherein the silica species comprises mono silicic acid and soluble polymeric silica.

3. The process of claim 2 wherein the silica species further comprises colloidal silica.

4. The process of claim 1 wherein the permeate stream and retentate stream are processed in continuous or discontinuous diafiltration.

5. The process of claim 4 wherein the number of diafiltrations is from 3 to 15.

6. The process of claim 1 further comprising isolating the product compound from the chromatographic product compound stream, wherein the final silica content of the product compound is less than about 0.1 percent by weight.

7. The process of claim 6 wherein the final silica content of the product compound is less than about 0.01 percent by weight.

8. The process of claim 7 wherein the final silica content of the product compound is less than about 0.005 percent by weight.

9. The process of claim 1 wherein the product compound is an x-ray contrast agent.

10. The process of claim 9 wherein the x-ray contrast agent is selected from iopamidol, iomeprol, iohexyl, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol.

11. The process of claim 1 wherein the product compound is a magnetic resonance imaging contrast agent.

12. The process of claim 11 wherein the magnetic resonance imaging contrast agent is selected from gadofosveset trisodium, gadoxdetate, gadomelitol, gadobenate dimeglumine, and the corresponding ligands thereof.

13. The process of claim 1 wherein the chromatographic apparatus is a reverse phase chromatographic apparatus.

14. The process of claim 13 wherein the stationary phase is silica based.

15. The process of claim 13 wherein the silica species having a molecular weight above the molecular weight cutoff of the membrane contained in the chromatographic silica stream is concentrated with reference to the chromatographic product compound stream and the product compound contained in the chromatographic product compound stream is concentrated with reference to the chromatographic silica stream.

16. The process of claim 13 wherein the weight ratio of the silica contained in the chromatographic silica stream to the silica contained in the chromatographic product compound stream is at least 2:1.

17. The process of claim 13 wherein the retentate is concentrated or dried prior to being loaded on the chromatographic apparatus.

18. A process for purifying a product solution comprising a product compound and polymeric silica, the process comprising loading the product solution on a reverse phase chromatographic apparatus containing a silica-based stationary phase and eluting one or more pre-fraction streams and one or more purified product fraction streams, wherein
the polymeric silica contained in the sum of the pre-fraction streams is concentrated with reference to the sum of the purified product fraction streams;
and the purified product compound contained in the sum of the purified product fraction streams is concentrated with reference to the sum of the pre-fraction streams.

19. The process of claim 18 wherein the polymeric silica comprises colloidal silica.

20. The process of claim 18 wherein the weight ratio of the silica contained in the sum of the pre-fraction streams to the silica contained in the sum of the purified product fraction streams is at least 2:1.

21. The process of claim 18 wherein the one or more purified product fraction streams further comprises monosilicic acid, and the one or more purified product fraction streams are further processed in a selective nanofiltration membrane apparatus to separate the purified product fraction streams into a permeate stream comprising the soluble silica species having a molecular weight below the molecular weight cut-off of the membrane and a retentate stream comprising the product compound and the soluble silica species having a molecular weight above the molecular weight cutoff of the membrane.

22. The process of claim 21 wherein the permeate stream and retentate stream are processed in continuous or discontinuous diafiltration.

23. The process of claim 22 wherein the number of diafiltrations is from 3 to 15.

24. The process of claim 21 further comprising isolating the product compound from the retentate stream, wherein the final silica content of the product compound is less than about 0.1 percent by weight.

25. The process of claim 24 wherein the final silica content of the product compound is less than about 0.01 percent by weight.

26. The process of claim 25 wherein the final silica content of the product compound is less than about 0.005 percent by weight.

27. The process of claim 18 wherein the product compound is an x-ray contrast agent.

28. The process of claim 27 wherein the x-ray contrast agent is selected from iopamidol, iomeprol, iohexyl, iopentol, iopromide, iosimide, ioversol, iotrolan, iotasul, iodixanol, iodecimol, ioglucamide, loglunide, iogulamide, iosarcol, ioxilan, iopamiron, metrizamide, iobitridol and iosimenol.

29. The process of claim 18 wherein the product compound is a magnetic resonance imaging contrast agent.

30. The process of claim 29 wherein the magnetic resonance imaging contrast agent is selected from gadofosveset trisodium, gadoxdetate, gadomelitol, gadobenate dimeglumine, and the corresponding ligands thereof.

31. A process for purifying a product solution comprising a product compound and polymeric silica, the process comprising loading the product solution on a reverse phase chromatographic apparatus containing a stationary phase and forming by separation a product compound stream comprising the product compound and a polymeric silica stream comprising the polymeric silica.

32. The process of claim 31 wherein the stationary phase is silica based.

33. The process of claim 31 wherein the polymeric silica contained in polymeric silica stream is concentrated with reference to the product compound stream and the product compound contained in the product compound stream is concentrated with reference to the polymeric silica stream.

34. The process of claim 31 wherein the polymeric silica comprises colloidal silica.

35. The process of claim 31 wherein the weight ratio of the silica contained in the polymeric silica stream to the silica contained in the product compound stream is at least 2:1.

36. The process of claim 31 wherein the product compound stream further comprises monosilicic acid, and the product compound stream is further processed in a selective nanofiltration membrane apparatus to separate the product compound stream into a permeate stream comprising the soluble silica species having a molecular weight below the molecular weight cut-off of the membrane and a retentate stream comprising the product compound and the soluble silica species having a molecular weight above the molecular weight cutoff of the membrane.

37. The process of claim 36 wherein the permeate stream and retentate stream are processed in continuous or discontinuous diafiltration.

38. The process of claim 37 wherein the number of diafiltrations is from 3 to 15.

39. The process of claim 36 further comprising isolating the product compound from the retentate stream, wherein the final silica content of the product compound is less than about 0.1 percent by weight.

40. The process of claim 39 wherein the final silica content of the product compound is less than about 0.01 percent by weight.

41. The process of claim 40 wherein the final silica content of the product compound is less than about 0.005 percent by weight.

42. The process of claim 31 wherein the product compound is an x-ray contrast agent.

43. The process of claim 42 wherein the x-ray contrast agent is selected from iopamidol, iomeprol, iohexyl, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol.

44. The process of claim 31 wherein the product compound is a magnetic resonance imaging contrast agent.

45. The process of claim 44 wherein the magnetic resonance imaging contrast agent is selected from gadofosveset trisodium, gadoxdetate, gadomelitol, gadobenate dimeglumine, and the corresponding ligands thereof.

* * * * *